(12) United States Patent  
Okihara

(10) Patent No.: US 11,090,442 B2  
(45) Date of Patent: Aug. 17, 2021

(54) SYRINGE CAP, SYRINGE ASSEMBLY, AND PREFILLED SYRINGE

(71) Applicant: TERUMO KABUSHIKI KAISHA, Tokyo (JP)

(72) Inventor: Hitoshi Okihara, Shizuoka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 216 days.

(21) Appl. No.: 15/715,562

(22) Filed: Sep. 26, 2017

(65) Prior Publication Data

US 2018/0015230 A1 Jan. 18, 2018

Related U.S. Application Data

(63) Continuation of application No. PCT/JP2016/059265, filed on Mar. 23, 2016.

(30) Foreign Application Priority Data

Mar. 26, 2015 (JP) .............................. JP2015-064348

(51) Int. Cl.
*A61M 5/32* (2006.01)
*A61M 5/31* (2006.01)

(52) U.S. Cl.
CPC ........ *A61M 5/3213* (2013.01); *A61M 5/3129* (2013.01); *A61M 5/3202* (2013.01);
(Continued)

(58) Field of Classification Search
CPC .. A61M 2005/3212; A61M 2005/3109; A61M 5/3213; A61M 5/3202; A61M 2205/0216
(Continued)

(56) References Cited

U.S. PATENT DOCUMENTS 5,980,495 A 11/1999 Heinz et al.
6,551,286 B1 * 4/2003 Claessens ........... A61M 5/3202
128/919

(Continued)

FOREIGN PATENT DOCUMENTS

JP 10-305098 11/1998
JP 2004-527361 9/2004
(Continued)

OTHER PUBLICATIONS

International Search Report and Written Opinion, PCT/JP2016/059265, Terumo Kabushiki Kaisha, 5 pages (dated Jun. 28, 2016).

*Primary Examiner* — Brandy S Lee
*Assistant Examiner* — Nidah M Hussain
(74) *Attorney, Agent, or Firm* — Foley & Lardner LLP

(57) ABSTRACT

A syringe cap is configured to be removably attached to a barrel to seal a needle hole in a puncture needle held by a barrel tip portion of the barrel, and comprises a first member that is configured to be pierced with the puncture needle and that comprises an elastic material having a Young's modulus in the range of 1 to 10 MPa; and a second member that comprises an elastic hollow body having a Young's modulus in the range of 1 to 10 MPa and that is configured form a closed space between the first member and the barrel. A vapor permeability of a material from which the first member is formed is lower than a vapor permeability of a material from which the second member is formed.

5 Claims, 4 Drawing Sheets

(52) U.S. Cl.
CPC ............... *A61M 2005/3109* (2013.01); *A61M 2005/3131* (2013.01); *A61M 2205/0216* (2013.01); *A61M 2207/00* (2013.01); *A61M 2209/10* (2013.01)

(58) Field of Classification Search
USPC ........................................................ 604/198
See application file for complete search history.

(56) References Cited

U.S. PATENT DOCUMENTS

| | | |
|---|---|---|
| 2004/0140285 A1 | 7/2004 | Vetter et al. |
| 2005/0027259 A1 | 2/2005 | Vetter et al. |
| 2008/0228136 A1* | 9/2008 | Seward ............. A61M 25/1002 604/96.01 |
| 2008/0303267 A1* | 12/2008 | Schnell ................. A61M 39/10 285/26 |
| 2010/0076382 A1* | 3/2010 | Weston ................. A61M 5/002 604/198 |
| 2013/0012886 A1* | 1/2013 | Kawachi ............. A61M 5/3202 604/192 |

FOREIGN PATENT DOCUMENTS

| | | |
|---|---|---|
| JP | 2004-305720 | 11/2004 |
| JP | 2005-230458 | 9/2005 |
| JP | 2009-534152 | 9/2009 |
| JP | 2014-162532 | 9/2014 |
| WO | WO-2007/125419 | 11/2007 |
| WO | WO-2011/114917 A1 | 9/2011 |

\* cited by examiner

SYRINGE CAP, SYRINGE ASSEMBLY, AND PREFILLED SYRINGE

CROSS-REFERENCE TO RELATED APPLICATIONS

The present application is a bypass continuation of PCT Application No. PCT/JP2016/059265, filed on Mar. 23, 2016, which claims priority to Japanese Application No. 2015-064348, filed on Mar. 26, 2015. The contents of these applications are hereby incorporated by reference in their entireties.

BACKGROUND

The present disclosure relates to a syringe cap, a syringe assembly, and a prefilled syringe.

In a prefilled syringe filled with a drug solution, for example, a syringe assembly includes a barrel tip portion having a puncture needle and a syringe cap having a tubular body with a closed distal end, which is removably attached to the barrel tip portion. In the syringe assembly, the syringe cap houses the puncture needle, the barrel tip portion, and the like in a housing space and accepts the puncture needle in a distal wall of the housing space to seal a needle hole. This configuration protects the puncture needle and prevents the drug solution and the like from leaking through the needle hole (See JP 10-305098 A, for example).

SUMMARY

The above syringe assembly is subjected to sterilization such as autoclave sterilization while the syringe cap is attached to the barrel tip portion, in other words, while the syringe cap houses the puncture needle and the like in a closed space formed by closing the housing space by the barrel tip portion. Therefore, in order to supply a sufficient amount of water vapor into the closed space and satisfactorily sterilize the puncture needle and the like, the syringe cap should preferably have high vapor permeability. Such a syringe cap, however, allows a drug solution that is filled in the barrel after sterilization to evaporate through the needle hole and the syringe cap, which may make it difficult to maintain the amount of the drug solution at the time of filling.

An object of certain embodiments described in this application is to provide a syringe cap that enables satisfactory sterilization of a puncture needle and the like and maintains the amount of a drug solution at the time of filling.

Another object is to provide a syringe assembly including the above syringe cap.

Yet another object is to provide a prefilled syringe including the above syringe assembly.

One embodiment is directed to a syringe cap removably attached to a barrel to seal a needle hole in a puncture needle held by a barrel tip portion of the barrel. The syringe cap includes: a first member that is configured to be pierced with accepting the puncture needle and being that is composed of an elastic material having a Young's modulus in the range of 1 to 10 MPa; and a second member that is composed of an elastic hollow body having a Young's modulus in the range of 1 to 10 MPa and that is configured to be capable of forming a closed space between the first member and the barrel, the second member being composed of an elastic hollow body having a Young's modulus in the range of 1 to 10 MPa, wherein the material for the first member formed from a material that has lower vapor permeability than the a material for forming the second member.

In the syringe cap, the first member sealing the needle hole in the puncture needle has lower vapor permeability than the second member forming the closed space for accommodating a part of the puncture needle that is not covered with the first member and the barrel tip portion. Accordingly, the syringe cap relatively easily allows water vapor to pass through the second member into the closed space, and prevents a drug solution filled in the barrel from evaporating from the needle hole through the first member. This enables satisfactory sterilization of the puncture needle and the barrel tip portion and maintains the amount of the drug solution at the time of filling.

In addition, in the syringe cap, the first member accepting the puncture needle has a Young's modulus in the range of 1 to 10 MPa, which ensures the sealing of the needle hole in the puncture needle. In addition, the second member surrounding the peripheral surface of the barrel has a Young's modulus in the range of 1 to 10 MPa, which facilitates removably attaching the syringe cap to the barrel and ensures an air-tight seal between the syringe cap and the barrel.

In the above syringe cap, the first member preferably has a vapor permeability of 250 $g/m^2 \cdot 0.24$ h or lower at 121° C., and the second member preferably has a vapor permeability of 400 $g/m^2 \cdot 24$ h or higher at 121° C. By setting a vapor permeability of the first member in this range, the drug solution filled in the barrel can be prevented from evaporating from the needle hole through the first member. In addition, by setting a vapor permeability of the second member in the above range, water vapor can enter the closed space in the syringe cap. The vapor permeability in this specification is measured in accordance with K7129 of JIS.

In one aspect, the second member has a tubular body with openings formed in a distal end side and a proximal end side, and the first member is disposed to close the opening in the distal end side of the second member. In this case, the tubular body of the second member facilitates a process for cleaning the inside of the tubular body by passing a liquid such as a cleaning water through the inside of the tubular body and a process for drying the inside of the tubular body. In addition, the syringe cap can be easily obtained by simply disposing the first member to close the opening in the distal end side of the second member from the outside.

In the above syringe cap, the second member may have a tubular body with a closed distal end and an opening in the proximal end, and the first member may be disposed on a distal end side in the second member. In this case, the entire body of the first member is in the second member, and therefore is subjected to the pressing force from the surrounding second member. This effectively prevents the first member from separating from the second member.

According to another embodiment of the present invention, there is provided a syringe assembly, including: the syringe cap; the barrel having the barrel tip portion; and the puncture needle held by the barrel tip portion, in which the syringe cap is removably attached to the barrel tip portion, and the distal end of the puncture needle has been pierced into the first member. By including the syringe cap, the syringe assembly having the advantageous effects described above can be obtained.

According to yet another embodiment of the present invention, there is provided a prefilled syringe, including: the syringe assembly; a drug solution filled in the barrel; and a gasket slidably inserted into the barrel. By including the syringe assembly, the prefilled syringe having the advantageous effects described above can be obtained.

DESCRIPTION OF EMBODIMENTS

Figure 1:
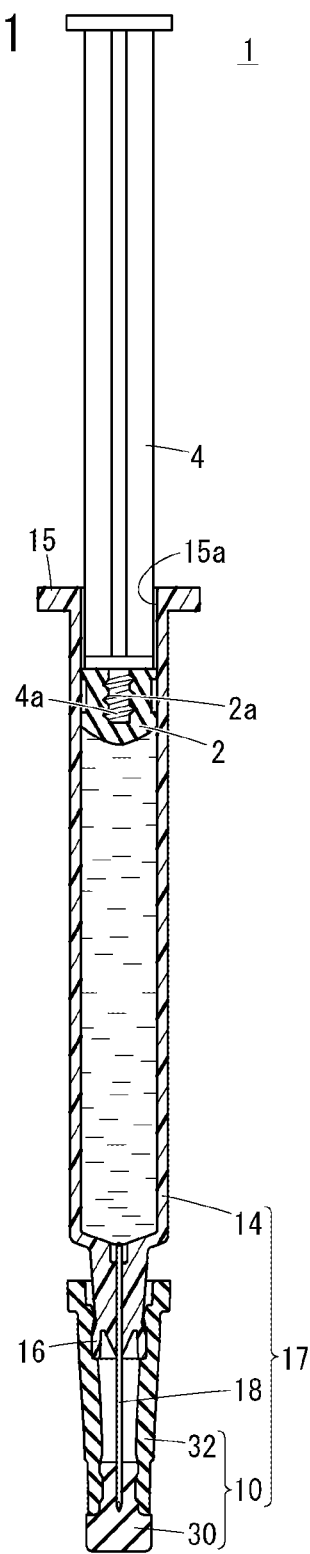
FIG. 1 is a vertical cross-sectional view of a prefilled syringe including a syringe assembly with a syringe cap attached to a barrel tip portion of a barrel according to an embodiment of the present invention.
Figure 2:
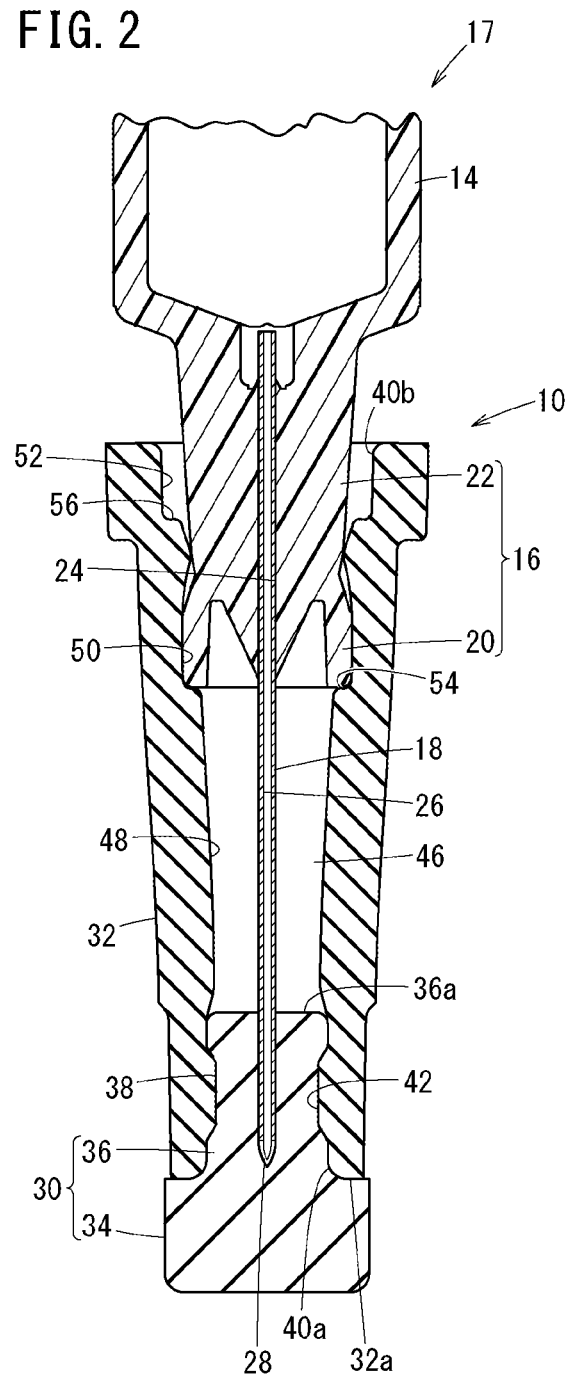
FIG. 2 is an enlarged cross-sectional view of a main part of the syringe assembly of FIG. 1.
Figure 3:
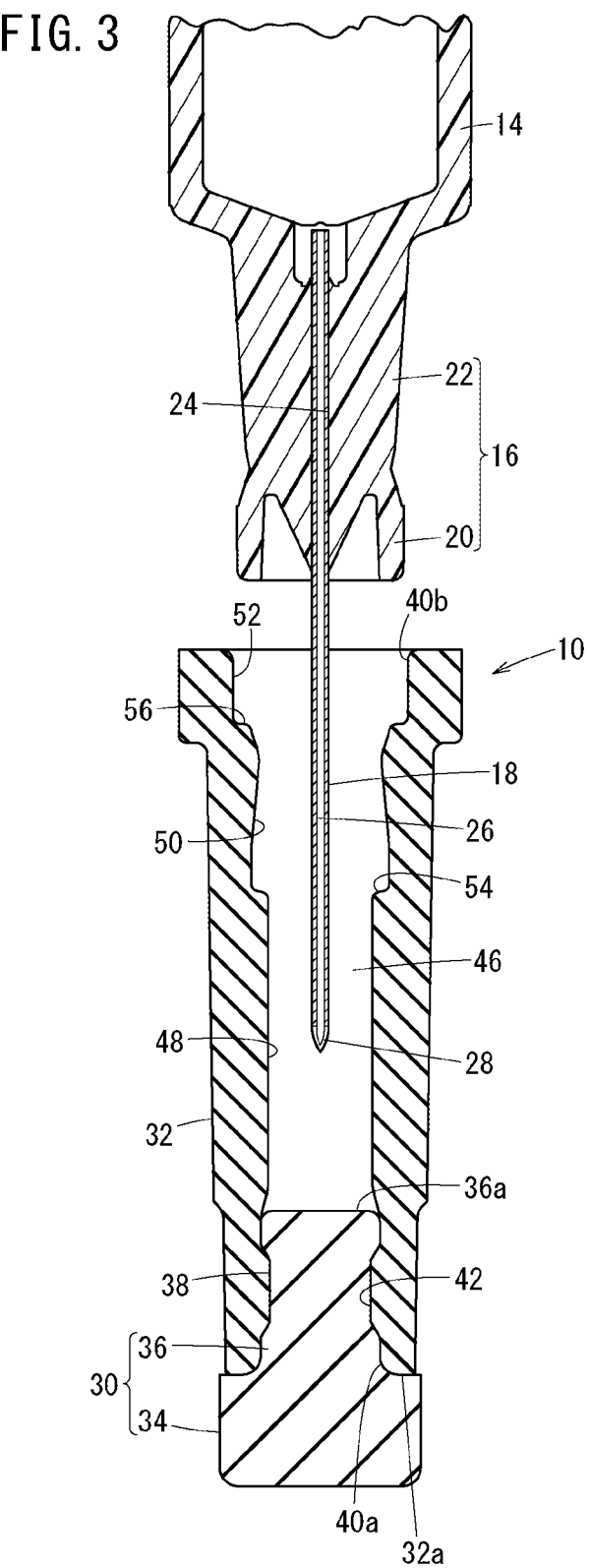
FIG. 3 is an enlarged cross-sectional view of a main part of the syringe cap for the syringe assembly of FIG. 2 before being attached to the barrel tip portion of the barrel.

Preferred embodiments of a syringe cap, a syringe assembly, and a prefilled syringe of the present invention will now be described with reference to the accompanying drawings. FIG. 1 is a vertical cross-sectional view of a prefilled syringe 1 according to an embodiment of the present invention. FIG. 2 is an enlarged cross-sectional view of a main part of a syringe assembly 17 according to the embodiment of the present invention. FIG. 3 is an enlarged view of a main part of a syringe cap 10 before being attached to a barrel tip portion 16 of a barrel 14 according to the embodiment of the present invention.

As shown in FIG. 1, the prefilled syringe 1 includes the syringe assembly 17 having the syringe cap 10 attached to the barrel tip portion 16 provided at a distal end of the barrel 14, a drug solution filled in an internal space in the barrel 14, a gasket 2 slidably disposed in the barrel 14, and a plunger 4 integrated with the gasket 2.

The barrel 14 has a transparent or translucent tubular body. The barrel 14 is preferably composed of a material having low oxygen permeability and a low vapor permeability, for example, polypropylene, polyethylene, polystyrene, polyamide, polycarbonate, polyvinyl chloride, poly-(4-methylpentene-1), acrylic resins, acrylonitrile-butadiene-styrene copolymers, polyester such as polyethylene terephthalate, various resins such as cyclic polyolefin, and glasses. The preferred materials among these materials are polypropylene and cyclic polyolefin in view of suitability for autoclave sterilization.

The barrel 14 includes a flange portion 15 projecting outward at the proximal end. The barrel 14 has an opening portion 15a on the inner side of the flange portion 15. The plunger 4 and the gasket 2 integrated with each other are inserted through the opening portion 15a. As shown in the figures, the gasket 2 has a recess 2a. The recess 2a has a female screw in its internal surface. The gasket 2 and the plunger 4 are integrated with each other by screwing a male screw formed in the distal end portion 4a of the plunger 4 into the female screw.

The barrel 14 includes, at the distal end, the barrel tip portion 16 having a smaller diameter than the diameter of the barrel 14. As shown in FIGS. 2 and 3, in this embodiment, the barrel tip portion 16 includes an annular head 20 having a generally constant outer diameter along its axis, and a tapered portion 22 having an increasing outer diameter toward the proximal end. The tapered portion 22 is disposed on the proximal end side of the annular head 20. In addition, the barrel tip portion 16 has a holding through-hole 24 along its axis. The barrel tip portion 16 holds a puncture needle 18 in the holding through-hole 24 to fix the position of the puncture needle 18. The puncture needle 18 may be fixed in the position by integrating the puncture needle 18 with the barrel 14 through insert molding, for example.

The puncture needle 18 is a linear hollow member, and projects from the barrel tip portion 16 toward the distal end while being held by the barrel tip portion 16. The puncture needle 18 has a needle hole 26 formed therethrough in the longitudinal direction. The needle hole 26 is in communication with the internal space in the barrel 14. In addition, the puncture needle 18 has a sharp edge 28 inclined with respect to the axis of the puncture needle 18 at the distal end portion. The distal end of the sharp edge 28 is the tip of the puncture needle 18.

The puncture needle 18 is preferably made of a material having an appropriate rigidity for penetrating the skin of a patient. Examples of the material for the puncture needle 18 include metals such as stainless steel, aluminium alloys, and titanium alloys, and hard resins such as polyphenylene sulfide. In order to reduce the puncture resistance generated when the puncture needle 18 penetrates the skin of a patient, the puncture needle 18 may be coated with lubricant at least in a part of the outer surface. Examples of the lubricant include liquid lubricants such as silicone oil The syringe cap 10 includes a first member 30, and a second member 32 having lower vapor permeability than the first member 30. The first member 30 is composed of an elastic material having a Young's modulus in the range of 1 to 10 MPa and a vapor permeability of 250 g/m$^2$·0.24 h or lower at 121° C., for example, butyl rubber. The first member 30 includes a generally cylindrical body 34 having a larger diameter than the outer diameter of the distal end side of the second member 32, and a plug portion 36 extending generally from the center of an end surface of the body 34 and having a slightly larger outer diameter than the inner diameter of the distal end side of the second member 32. The plug portion 36 has a reduced-diameter portion 38 generally in the middle of the peripheral surface in the extending direction. The reduced-diameter portion 38 has a smaller diameter than the diameter of the other part of the plug portion 36.

The second member 32 is composed of an elastic material having a Young's modulus in the range of 1 to 10 MPa and a vapor permeability of 400 g/m$^2$·24 h or higher at 121° C., for example, isoprene rubber. The second member 32 has a hollow body with an opening in the distal end side and an opening in the proximal end side. The second member 32 has an annularly raised portion 42 on the inner wall of an opening 40a in the distal end side. The annularly raised portion 42 engages with the reduced-diameter portion 38.

The syringe cap 10 has a tubular body with a closed distal end formed by the first member 30 disposed to close the opening 40a in the distal end side of the second member 32. Specifically, the plug portion 36 of the first member 30 is press fitted into the second member 32 through the opening 40a until the end surface of the body extending from the plug portion 36 comes into contact with a distal end surface 32a of the second member 32. In this way, the first member 30 is integrated with the second member 32, which defines the syringe cap 10 with a closed distal end. In the syringe cap 10 assembled in this way, the reduced-diameter portion 38 is engaged with the annularly raised portion 42 so that the first member 30 is firmly fixed to the second member 32.

The syringe cap 10 has a housing space 46 extending along the center of its axis. The housing space 46 is formed by an end surface 36a of the plug portion 36 of the first member 30, and the inner wall of the second member 32. Apart of the puncture needle 18 and a part of the barrel tip portion 16 are inserted into the housing space 46 until the puncture needle 18 goes into the first member 30 from the side of the plug portion 36 toward the side of the body 34. In addition, when the barrel tip portion 16 is disposed to close the opening 40b at the proximal end of the housing space 46, a closed space is formed between the first member 30 surrounded by the second member 32 and the barrel tip portion 16.

The housing space 46 has different inner diameters in a small-diameter area 48, a medium-diameter area 50, and a large-diameter area 52, which are disposed in this order from the end surface 36a toward the proximal end side. The inner diameter in the medium-diameter area 50 is smaller than the outer diameter of the annular head 20. At the distal end of the medium-diameter area 50, a stopper portion 54 is provided. The second member 32 has the smallest inner diameter in the small-diameter area 48 extending from the stopper portion 54 toward the distal end side. The inner diameter in the small-diameter area 48 is larger than the outer diameter of the puncture needle 18 and smaller than the inner diameter in the medium-diameter area 50. The inner diameter in the large-diameter area 52 is larger than the outer diameter of the annular head 20.

In this embodiment, the stopper portion 54 is formed by the difference between the inner diameter in the small-diameter area 48 and the inner diameter in the medium-diameter area 50. The barrel tip portion 16 is inserted into the housing space 46 until the distal end surface of the barrel tip portion 16 comes into contact with the stopper portion 54. The stopper portion 54 thus defines a final insertion position of the barrel tip portion 16 and the length of the insertion of the puncture needle 18 into the first member 30. That is, the stopper portion 54 prevents the barrel tip portion 16 from further entering the housing space 46 beyond the final insertion position of the barrel tip portion 16.

In addition, a temporary stopper portion 56 is formed between the medium-diameter area 50 and the large-diameter area 52. The temporary stopper portion 56 has a function of, when the barrel tip portion 16 is inserted into the housing space 46 toward the final insertion position to removably attach the syringe cap 10 to the barrel tip portion 16, temporarily preventing the barrel tip portion 16 from entering the housing space 46. The temporary stopper portion 56 may be omitted.

In this embodiment, the syringe cap 10 is removably attached to the barrel tip portion 16. Alternatively, in a modification of the syringe cap 10, the syringe cap may removably be attached to the distal end portion of the barrel 14 not to the barrel tip portion 16.

The syringe cap 10 of this embodiment has the basic structure described above. The advantageous effects of the syringe cap 10 will now be described.

The first member 30 and the second member 32 are separately formed by injection molding, for example, and then cleaned. Since the second member 32 is open at both ends, a cleaning liquid (water) or the like can easily flow through the second member 32. In other words, the second member 32 is easy to clean.

Thereafter, drying is performed. Since the second member 32 is open at both ends, the cleaning liquid can easily drain to the outside of the second member 32 through the openings 40a and 40b. Thus the second member 32 is easy to dry, too.

After the cleaning process, as described above, the plug portion 36 of the first member 30 is press fitted into the openings 40a in the second member 32, and the syringe cap 10 is obtained.

The syringe cap 10 is then removably attached to the barrel tip portion 16 of the barrel 14. As shown in FIG. 3, the relative position between the syringe cap 10 and the barrel 14 is adjusted such that the center of the axis of the puncture needle 18 is aligned with the center of the axis of the housing space 46 and the distal end of the puncture needle 18 faces the opening 40b in the proximal end side of the syringe cap 10. Then, the syringe cap 10 and the barrel 14 are relatively moved toward each other along the center of their axes so that the puncture needle 18 and the barrel tip portion 16 of the barrel 14 are inserted into the housing space 46.

The puncture needle 18 and the barrel tip portion 16 are inserted into the large-diameter area 52, in which the inner diameter is larger than in the medium-diameter area 50 and the small-diameter area 48, and the distal end surface of the annular head 20 comes into contact with the temporary stopper portion 56 before being inserted into the medium-diameter area 50 and the small-diameter area 48. Insertion of the puncture needle 18 and the barrel tip portion 16 is temporarily stopped to ensure that the center of the axis of the housing space 46 is generally aligned with the center of the axis of the puncture needle 18.

As the puncture needle 18 and the barrel tip portion 16 are inserted further, the annular head 20 goes beyond the temporary stopper portion 56 into the medium-diameter area 50. At this time, the outer surface of the annular head 20 is in intimate contact with the inner surface in the medium-diameter area 50, which makes an air-tight seal between the medium-diameter area 50 and the barrel tip portion 16. At the same time, the distal end of the puncture needle 18 then goes into the first member 30 from the side of the plug portion 36 toward the side of the body 34.

Then, as shown in FIG. 1, when the annular head 20 reaches the final insertion position at the end of the medium-diameter area 50, the distal end surface of the annular head 20 comes into contact with the stopper portion 54. As a result, the barrel tip portion 16 is prevented from entering the housing space 46 any further, and the syringe cap 10 is attached to the barrel 14 at the predetermined position. Accordingly, the syringe assembly 17 with a closed space in the small-diameter area 48 can be obtained.

As described above, in the syringe assembly 17, the first member 30 accepting the puncture needle 18 has a Young's modulus in the range of 1 to 10 MPa, which ensures the sealing of the needle hole 26 in the puncture needle 18. In addition, the second member 32 surrounding the peripheral surface of the barrel 14 has a Young's modulus in the range of 1 to 10 MPa, which facilitates removably attaching the syringe cap 10 to the barrel 14 and ensures formation of an air-tight seal between the syringe cap 10 and the barrel 14.

The syringe assembly 17 is subjected to sterilization in this state. That is, the syringe assembly 17 is subjected to autoclave sterilization using water vapor at a high temperature and under a high pressure, for example.

As described above, in the syringe cap 10, the first member 30 sealing the needle hole 26 in the puncture needle 18 has lower vapor permeability than the second member 32 surrounding a part of the puncture needle 18 that is not covered with the first member 30 and the barrel tip portion 16. Accordingly, water vapor can easily pass through the second member 32 into the closed space inside. In other words, the syringe cap 10 relatively easily allows water vapor to enter the closed space. This enables satisfactory sterilization of the puncture needle 18 and the barrel tip portion 16 in the syringe cap 10.

In addition, the prefilled syringe 1 is made by filling the barrel 14 with a drug solution and then inserting the plunger 4 with the gasket 2 into the barrel 14. As described above, in the prefilled syringe 1, the first member 30 sealing the needle hole 26 in the puncture needle 18 has lower vapor permeability, which prevents the drug solution from evaporating through the first member 30. This enables satisfactory sterilization of the puncture needle 18 and the barrel tip portion 16 and maintains the amount of the drug solution at the time of filling. In addition, the first member 30 and the second member 32 of this embodiment have vapor permeability in the range described above, which further effectively achieves the advantageous effects described above.

Figure 4:
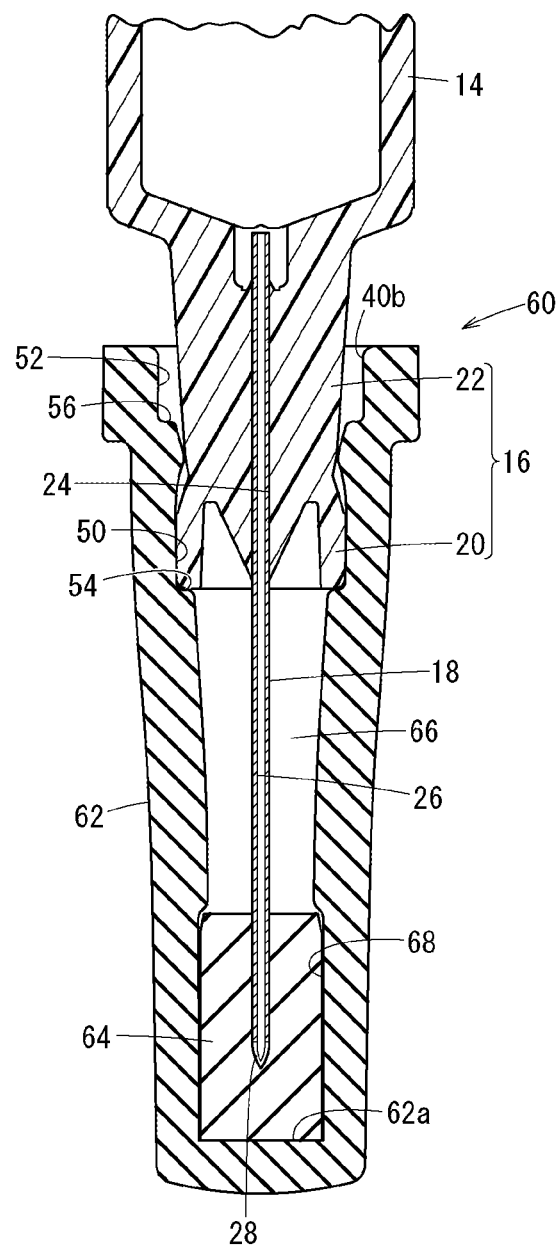
FIG. 4 is an enlarged cross-sectional view of a main part of a syringe cap according to a modification attached to the barrel tip portion of the barrel.

As described above, the syringe cap 10 of this embodiment includes the first member 30 having the plug portion 36 and the body 34, and the tubular second member 32, which are integrated with each other. Alternatively, as shown in FIG. 4, a modified syringe cap 60 may include a second member 62 with a closed distal end, and a first member 64 disposed on a distal end wall 62a side in the second member 62. In FIG. 4, the components having the same or similar functions or effects as or to the counterpart components in FIG. 1 are provided with the same reference numerals and their detailed description will be omitted.

The second member 62 is composed of a material similar to the material for the second member 32 and has a tubular body with an opening 40b only in the proximal end side and a closed distal end. The second member 62 has a housing space 66, and a widened-diameter area 68 near the distal end side of the housing space 66. In the widened-diameter area 68, the second member 62 has a larger diameter than in the middle area.

The first member 64 is composed of a material similar to the material for the first member 30 and has a cylindrical body having a slightly larger outer diameter than the inner diameter of the distal end side of the second member 62. The first member 64 is press fitted into the second member 62 through the opening 40b until the first member 64 comes into contact with the distal end wall 62a of the second member 62, so that the first member 64 is safely locked in the widened-diameter area 68 in the housing space 66. This configures the syringe cap 60 including the first member 64 and the second member 62 integrated with each other.

As in the above syringe cap 10, the syringe cap 60 according to the modification can removably be attached to the barrel tip portion 16 of the barrel 14. The first member 64 accepts the puncture needle 18 and the second member 62 has a closed space inside. Accordingly, this modification also enables satisfactory sterilization of the puncture needle 18 and the barrel tip portion 16 and maintains the amount of a drug solution at the time of filling.

In addition, as described above, in the syringe cap 60 according to the modification, the cylindrical first member 64 is disposed in the second member 62 having a tubular body with a closed distal end without being exposed to the outside of the syringe cap 60, which further effectively prevents the second member 62 from separating from the first member 64.

The syringe cap of the present invention is not limited to the syringe caps 10 and 60 with the structures described above, and may be any syringe caps in which the second member capable of forming the closed space has higher vapor permeability than the first member accepting the puncture needle 18. In addition, the first member and the second member may be integrated with each other by insert molding, for example.

Certain embodiments of the present invention have been described above. However, the present invention is not limited to these embodiments. Rather, the above-described embodiments can be modified without departing from the scope of the present invention.

What is claimed is:

1. A syringe cap configured to be removably attached to a barrel to seal a needle hole in a puncture needle held by a barrel tip portion of the barrel, the syringe cap comprising:
a first member that is configured to be pierced with the puncture needle and that comprises an elastic material having a Young's modulus in the range of 1 to 10 MPa; and
a second member that comprises an elastic hollow body having a Young's modulus in the range of 1 to 10 MPa and that is configured to form a closed space between the first member and the barrel,
wherein a water vapor permeability of a material from which the first member is formed is 250 $g/m^2 \cdot 24$ h or lower at 121° C., and a water vapor permeability of a material from which the second member is formed is 400 $g/m^2 \cdot 24$ h or higher at 121° C.

2. The syringe cap according to claim 1, wherein:
the second member comprises a tubular body with a distal opening at a distal end side of the tubular body and a proximal opening at a proximal end side of the tubular body, and
the first member is disposed to close the opening in the distal end side of the second member.

3. The syringe cap according to claim 1, wherein:
the second member comprises a tubular body with a closed distal end side and an opening in a proximal end side, and
the first member is disposed in the second member at the closed distal end side of the second member.

4. A syringe assembly, comprising:
the syringe cap according to claim 1;
the barrel comprising the barrel tip portion; and
the puncture needle held by the barrel tip portion,
the syringe cap is removably attached to the barrel tip portion, and a distal end of the puncture needle is pierced into the first member.

5. A prefilled syringe, comprising:
the syringe assembly according to claim 4;
a drug solution filled in the barrel; and
a gasket slidably disposed in the barrel.

* * * * *